(12) United States Patent
Mitchell

(10) Patent No.: US 10,453,237 B2
(45) Date of Patent: Oct. 22, 2019

(54) AUTOMATIC VIEWPORT RELEVELING

(71) Applicant: INTERNATIONAL BUSINESS MACHINES CORPORATION, Armonk, NY (US)

(72) Inventor: Robert John Mitchell, Mississauga (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/850,982

(22) Filed: Dec. 21, 2017

(65) Prior Publication Data

US 2019/0197745 A1 Jun. 27, 2019

(51) Int. Cl.
| | |
|---|---|
| *G06T 11/60* | (2006.01) |
| *G06T 3/40* | (2006.01) |
| *G06F 3/048* | (2013.01) |
| *G16H 30/40* | (2018.01) |
| *H04N 1/60* | (2006.01) |
| *H04N 5/57* | (2006.01) |
| *H04N 9/64* | (2006.01) |
| *H04N 9/73* | (2006.01) |
| *G09G 5/02* | (2006.01) |
| *G06F 3/0484* | (2013.01) |

(52) U.S. Cl.
CPC .......... *G06T 11/60* (2013.01); *G06F 3/04845* (2013.01); *G06F 3/04847* (2013.01); *G06T 3/40* (2013.01); *G16H 30/40* (2018.01); *G06F 2203/04805* (2013.01); *G06F 2203/04806* (2013.01); *G06T 2210/41* (2013.01)

(58) Field of Classification Search
USPC ........................................... 345/589
See application file for complete search history.

(56) References Cited

U.S. PATENT DOCUMENTS

| | | |
|---|---|---|
| 7,058,901 B1 | 6/2006 | Haffey et al. |
| 7,236,637 B2 * | 6/2007 | Sirohey ................. G06T 3/4084 382/240 |
| 8,520,017 B2 | 8/2013 | Kondo et al. |

(Continued)

FOREIGN PATENT DOCUMENTS

CN 102525523 3/2016

OTHER PUBLICATIONS

Haraguchi, D. et al., "A Web-based image viewer for multiple PET-CT follow-up studies," 33rd Annual International Conference of the IEEE EMBS, Boston, Massachusetts USA, Aug. 30-Sep. 3, 2011.

*Primary Examiner* — Wesner Sajous
(74) *Attorney, Agent, or Firm* — Michael Best & Friedrich LLP

(57) ABSTRACT

A computer-implemented process for automatic viewport re-leveling, in response to receiving a medical digital image, overlays the medical digital image with a floating viewport sized to represent a subset of the image to be viewed in a first instance. A limited set of brightness values is re-allocated to a set of pixels, within the subset of the image in the floating viewport that is less than a set of pixels in the medical digital image, in a second instance automatically. Responsive to the re-allocation, detail of local features within the subset of the image within the floating viewport in the second instance is accentuated.

20 Claims, 5 Drawing Sheets

Process 500

Start 502

↓

In response to receiving a medical digital image representative of a portion of a scan of a patient, overlay the image with a floating viewport sized to represent a subset of the image as a region to be viewed in a first instance
504

↓ re-allocate a limited set of brightness values associated with an output device to a reduced set of pixels associated with the region within the floating viewport in a second instance automatically
506

↓ responsive to the re-allocation, accentuate detail of local features within the region within the floating viewport in the second instance
508

↓

End 510

(56) References Cited

U.S. PATENT DOCUMENTS

| | | | |
|---|---|---|---|
| 8,971,598 B2 | 3/2015 | Lavi et al. | |
| 9,078,565 B2 | 7/2015 | Profio et al. | |
| 2002/0057850 A1* | 5/2002 | Sirohey | G06T 3/4084 |
| | | | 382/299 |
| 2016/0345925 A1* | 12/2016 | Westerhoff | A61B 6/5223 |
| 2017/0287174 A1* | 10/2017 | Muslih | G06T 11/005 |
| 2018/0161008 A1* | 6/2018 | Huepf | A61B 8/462 |

* cited by examiner

Viewport management system
300

AUTOMATIC VIEWPORT RELEVELING

BACKGROUND

The present invention relates generally to displaying medical digital images in a graphical user interface of a data processing system, and more specifically, to automatic viewport releveling in the graphical user interface of the data processing system.

In a typical example, a medical digital image may be produced as a result of a computed tomography (CT) scan comprises a matrix of pixels with each pixel having a CT number, that is converted into a visible image of grey shades. The visible image thus created depends upon settings for a window width, a window level, zoom control and other factors. An area of the medical digital image that is actually displayed is controlled by the zoom control.

Using the example above, the window width is a range of CT numbers displayed using shades of gray, ranging from black to white. CT numbers greater than the window width are displayed as white, while CT numbers, less than the window width, are displayed as black. The window width control adjusts a range of CT numbers that are displayed with contrast. Reducing the window width increases the image contrast. The window level defines a center of the scale of the range of CT numbers. The CT scan has very high contrast sensitivity enabling a window setting to enhance very small density differences for scanned tissues. Because a CT machine can detect a difference in scanned tissues of less than 1% a small density resolution difference, as measured by the CT scan, is exaggerated to permit viewing on a display of a computer by users that do not have a capability to perceive the subtle differences produced.

When displaying the medical digital image, pixel values represented in a computer typically in a range of values between 0 and a predetermined maximum are allocated a particular brightness value for rendering on a display of the computer. A correspondence between the pixel values and display brightness levels is typically achieved using a look up table, which in some cases is a simple linear translation. Using the lookup table, each pixel provided in an input image is mapped or transformed to a corresponding pixel in an output image to specify a new pixel value in place of an original pixel value. Previous examples of displaying medical digital images, including viewing a CT scan, in which window/level parameters are critical to a practitioner's ability to discern features of interest, typically compute image features across a breadth of the image. However, when computed image-wide, local features are typically not presented with sufficient relief, and often introduce a significant delay during refreshing.

In another previous example of displaying a medical digital image, a display comprises three rows of images in which each row is a slice sequence of a particular scan from a number of slices. A middle row, deemed a primary row, contains a scan selected by a user at a time tn, a corresponding top row contains scans from a time tn−1 and a corresponding bottom row contains scans from a time tn+1. The images are displayed in a fixed grid arrangement.

In another previous example of displaying a medical digital image, use of a zoom tool displays an image, which is a smaller region of a corresponding high-resolution full size image. In yet another previous example of displaying a medical digital image, sub-regions of a larger high-resolution image have not been allocated sufficient contrast so that all contours and image features are visible.

In yet another previous example of displaying a medical digital image, visualizing a region of interest within a viewport presents image data as an image in the viewport using a set of global image processing operations and a viewing window in the viewport. A second and different set of image processing operations is provided for the viewing window that reduces image artifact with respect to a desired structure of interest in the viewing window in the viewport.

In yet another previous example of displaying a medical digital image, display mode data for each classified kind of a medical image indicates, based on the positions of the medical images set in the display mode by the user, at least a number of screen divisions, display positions formed by the screen divisions, and an indication of the classified kind of each of plural of medical images formed within the screen divisions. Each display position corresponds to a single classified kind of medical image when medical images corresponding to different classified kinds are concurrently displayed on a screen. An image display unit is configured to display respective medical images included in obtained image files on the screen in accordance with display mode data added in the obtained image files.

Within a context of these previous examples, general releveling tools are known, however none typically provide additional insight available for local features needed to discern the features of interest.

SUMMARY

According to an embodiment of the present disclosure, a computer-implemented process for automatic viewport re-leveling, in response to receiving a medical digital image, overlays the medical digital image with a floating viewport sized to represent a subset of the image to be viewed in a first instance. A limited set of brightness values is re-allocated to a set of pixels, within the subset of the image in the floating viewport that is less than a set of pixels in the medical digital image, in a second instance automatically. Responsive to the re-allocation, detail of local features within the subset of the image within the floating viewport in the second instance is accentuated.

BRIEF DESCRIPTION OF THE DRAWINGS

For a more complete understanding of this disclosure, reference is now made to the following brief description, taken in conjunction with the accompanying drawings and detailed description, wherein like reference numerals represent like parts.

DETAILED DESCRIPTION

Figure 1:
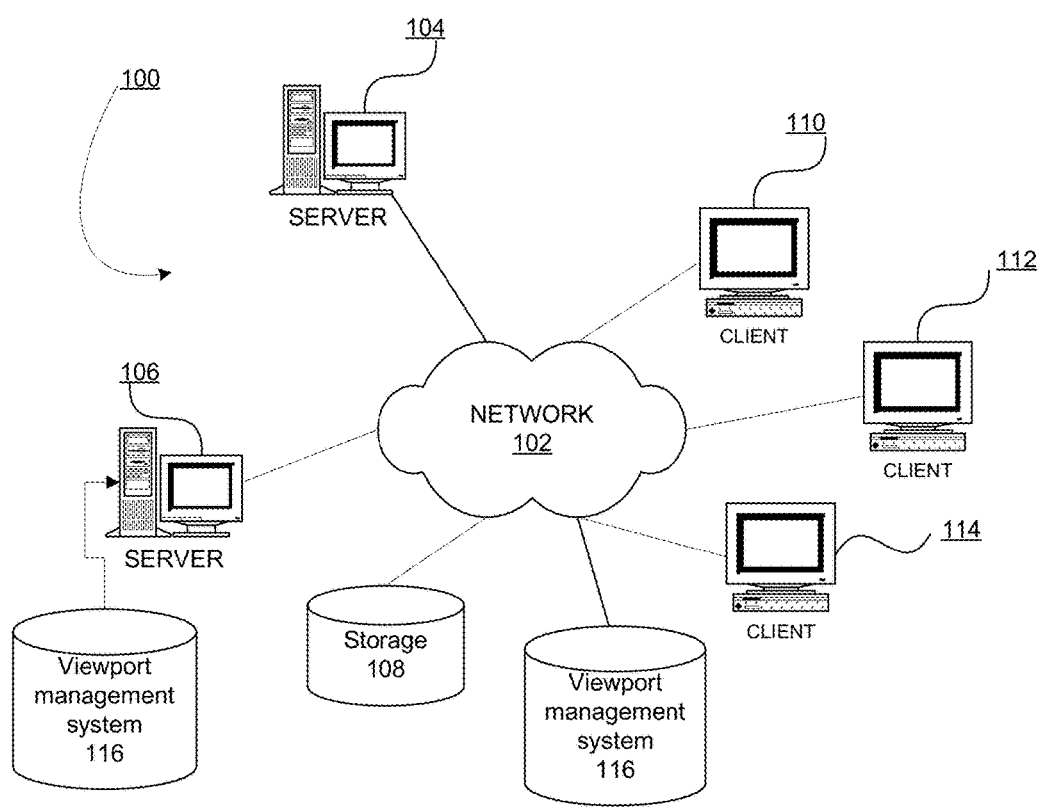
FIG. 1 is a block diagram of a network data processing system operable for various embodiments of the disclosure.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
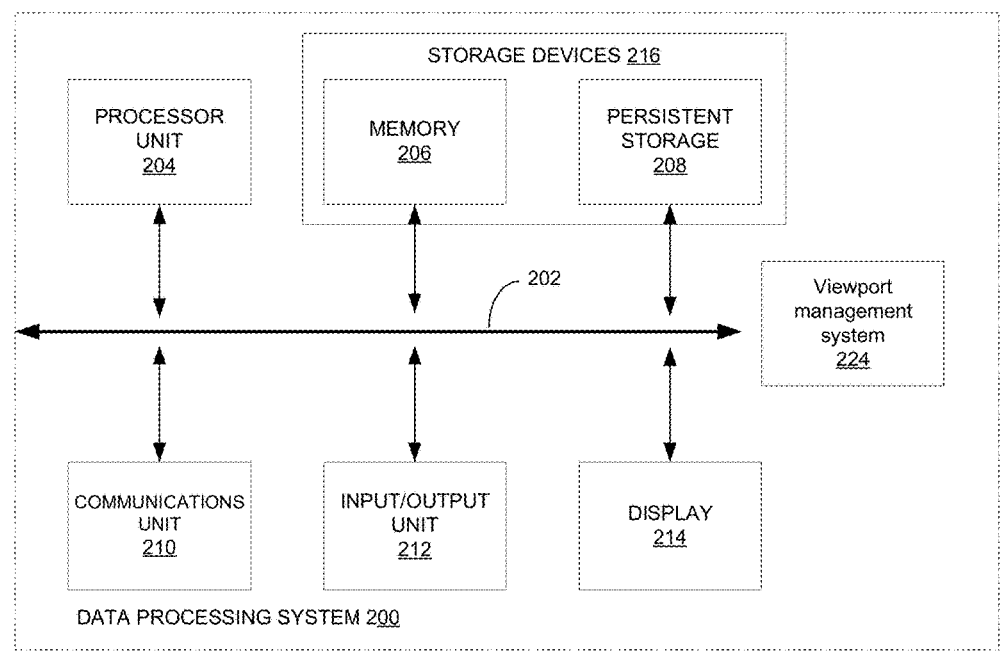
FIG. 2 is a block diagram of a data processing system in the network data processing system of FIG. 1 operable for various embodiments of the disclosure.
Figure 2:
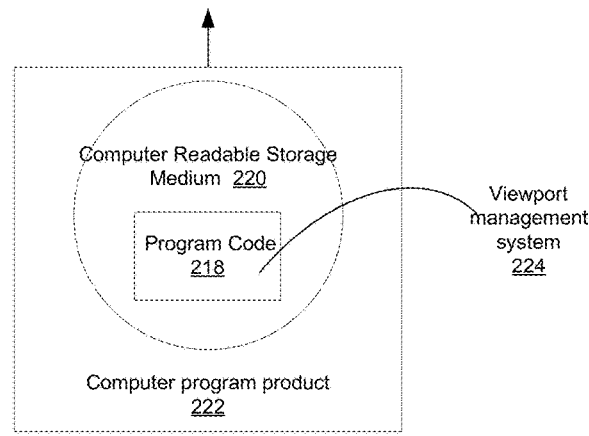

With reference now to the Figures and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, viewport management system 116 and applications to clients 110, 112, and 114. Clients 110, 112, and 114 are clients to server 104 in this example. In addition of a process using viewport management system 116 may also be directly connected to network 102. Network data processing system 100 may include additional servers, clients, and other devices not shown.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

With reference to FIG. 2 a block diagram of an exemplary data processing system operable for various embodiments of the disclosure is presented. In this illustrative example, data processing system 200 includes communications fabric 202, which provides communications between processor unit 204, memory 206, persistent storage 208, communications unit 210, input/output (I/O) unit 212, display 214 and viewport management system 224.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices 216. A storage device is any piece of hardware that is capable of storing information, such as, for example without limitation, data, program code in functional form, and/or other suitable information either on a temporary basis and/or a permanent basis. Memory 206, in these examples, may be, for example, a random access memory or any other suitable volatile or non-volatile storage device.

Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208. In another example, viewport management system 224 may also be contained within memory 206 or persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard, a mouse, and/or some other suitable input device. Further, input/output unit 212 may send output to a printer. Display 214 provides a mechanism to display information to a user.

Instructions for the operating system, applications and/or programs may be located in storage devices 216, which are in communication with processor unit 204 through communications fabric 202. In these illustrative examples the instructions are in a functional form on persistent storage 208. These instructions may be loaded into memory 206 for execution by processor unit 204. The processes of the different embodiments may be performed by processor unit 204 using computer-implemented instructions, which may be located in a memory, such as memory 206.

These instructions are referred to as program code, computer usable program code, or computer readable program code that may be read and executed by a processor in processor unit 204. The program code in the different embodiments may be embodied on different physical or tangible computer readable storage media, such as memory 206 or persistent storage 208.

Program code 218 is located in a functional form on computer readable storage media 220 that is selectively removable and may be loaded onto or transferred to data processing system 200 for execution by processor unit 204. Program code 218 and computer readable storage media 220 form computer program product 222 in these examples. In one example, computer readable storage media 220 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable storage media 220 also may take the form of a persistent storage, such as a hard drive, a thumb drive, or a flash memory that is connected to data processing system 200. The tangible form of computer readable storage media 220 is also referred to as computer recordable storage media or a computer readable data storage device. In some instances, computer readable storage media 220 may not be removable. In one example, program code 218 contains program code which when executed causes viewport management system 224 to be fully functional.

Alternatively, program code 218 may be transferred to data processing system 200 from computer readable storage media 220 through a communications link to communications unit 210 and/or through a connection to input/output unit 212. The communications link and/or the connection may be physical or wireless in the illustrative examples.

In some illustrative embodiments, program code 218 may be downloaded over a network to persistent storage 208 from another device or data processing system for use within data processing system 200. For instance, program code stored in a computer readable data storage device in a server data processing system may be downloaded over a network from the server to data processing system 200. The data processing system providing program code 218 may be a server computer, a client computer, or some other device capable of storing and transmitting program code 218.

Using the example of data processing system 200, a computer-implemented process for automatic viewport re-leveling, in response to receiving a medical digital image by processor unit 204, overlays the medical digital image with a floating viewport sized to represent a subset of the image to be viewed in a first instance. A limited set of brightness values is re-allocated by processor unit 204 to a set of pixels, within the subset of the image in the floating viewport that is less than a set of pixels in the medical digital image, in a second instance automatically. Responsive to the re-allocation, detail of local features within the subset of the image within the floating viewport in the second instance is accentuated by processor unit 204.

The description, which follows, and the embodiments described therein, is provided by way of illustration of an example, or examples, of particular embodiments of the principles of the present invention. These examples are provided for the purposes of explanation, and not limitation, of those principles and of the invention. In the description, which follows, like parts are marked throughout the specification and the drawings with the same respective reference numerals.

The following detailed description of the embodiments of the present invention does not limit the implementation of the present invention to any particular data processing system programming language. The present invention may be implemented in any data processing system programming language provided that the OS (Operating System) provides the facilities that may support the requirements of the embodiments of the present invention. Any limitations presented may be quite likely a result of a particular type of OS, data processing system programming language, or data processing system and may not be a limitation of the embodiment of the present invention.

Figure 3:
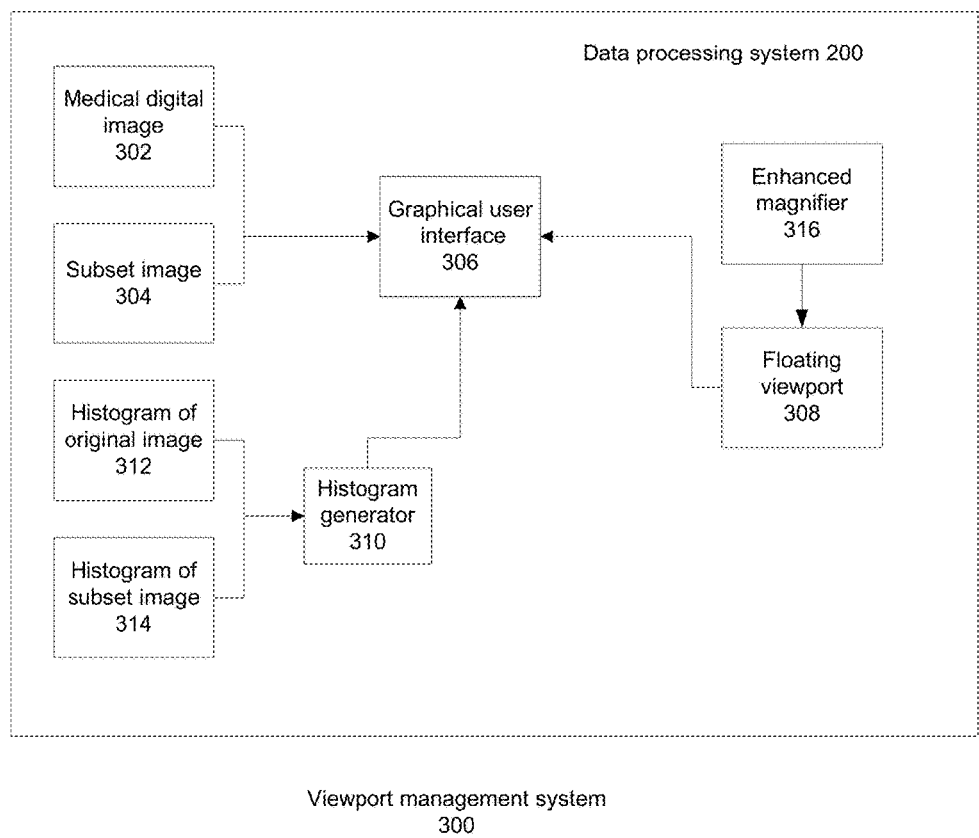
FIG. 3 is a block diagram representation of a viewport management system operable for various embodiments of the disclosure.

FIG. 3 is a block diagram of components of a viewport management system in accordance with one embodiment of the disclosure. Viewport management system 300 leverages operation support of underlying components of a data processing system on which it depends, for example data processing system 200 of FIG. 2.

Medical digital image 302 represents a set of images, which are representative of one of more scans of portions of a patient. Differing scanning technologies used typically result in use of a corresponding one of the image modalities associated with a respective scan technique. Medical digital image 302 is a full medical digital image. In contrast with the full medical digital image, subset image 304 represents a particular portion of the full medical digital image selected by a user using floating viewport 308 in graphical user interface 306. Subset image 304 may also be referred to as a sub-region or a region of interest.

When medical digital image 302 is being reviewed, a radiologist typically wants to view a sub-section of a full image in more detail. Use of a magnifier tool, for example, enhanced magnifier 316, provides an increase in spatial detail of a region of interest for the user. Enhanced magnifier 316 is an example of a software module capable of magnifying a selected portion of an image, however it has additional capability as presented in the context of viewport management system 300.

However, to improve differentiation of gray levels of medical digital image 302, it is necessary to identify subset image 304 also referred to as a region of interest (ROI). Subset image 304 identified may contain a narrower set of gray levels. Histogram generator 310 calculates a histogram of values for medical digital image 302 as histogram of original image 312. Histogram generator 310 also recalculates a histogram of values in subset image 304 identified to create histogram of subset image 314. The values in subset image 304 identified are reallocated to an entire displayable window width (for example, 255 levels) to provide a possibility of much greater detail when viewed in graphical user interface 306. Enhanced magnifier 316 provides a capability of a combination of re-sampling of subset image 304 identified within floating viewport 308 generated by enhanced magnifier 316.

Figure 4:
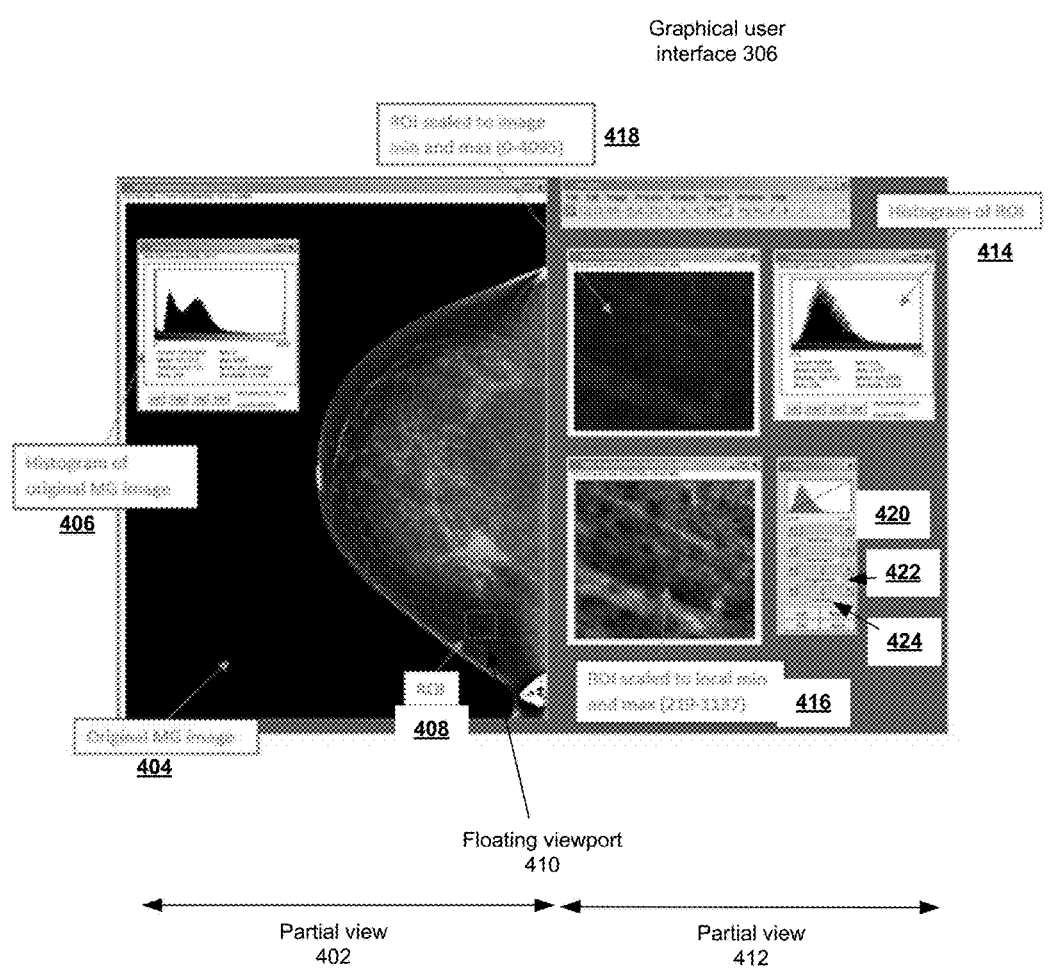
FIG. 4 is a pictorial representation of display of a graphical user interface used in an example of the viewport management system 300 of FIG. 3 in accordance with one embodiment of the disclosure.

FIG. 4 is a pictorial representation of display of graphical user interface used in example of viewport management system 300 of FIG. 3 in accordance with one embodiment of the disclosure. With reference to FIG. 4, graphical user interface 306 of FIG. 3 displays a partial view 402 of original MG image 404 representing a digital mammography image obtained from a previous scan of a patient. Histogram of original MG image 406 displays a result of a calculation of a distribution of values for the complete digital mammography image. Region of interest (ROI) 408 refers to a particular portion of original MG image 404 within floating viewport 410 (area bounded by small rectangle). When medical images are being reviewed, radiologists typically want to view a particular sub-region, in this example, ROI 408 of original MG image 404 in more detail. Use of a magnifier tool further provides an increase in spatial detail of ROI 408 for the user.

However, an improvement in differentiation of gray levels requires identification of a sub-region, in this example ROI 408. Partial view 412 includes histogram of ROI 414 that displays a result of a calculation of a distribution of values for only the sub-region, ROI 408. One can readily observe a difference between histogram of original MG image 406 and histogram of ROI 414. The difference is typically a result of ROI 408 containing a narrower set of gray levels than original MG image 404. Recalculating a histogram of values in ROI 408 and reallocating those values from the sub-region ROI 408 to an entire displayable window width (for example, 255 levels) provides a possibility of much greater detail, as shown in ROI scaled to local min and max (219-1137) 416 when compared with what is shown in ROI scaled to image min and max (0-4095) 418.

In a further refinement of the above, additional manual controls 420 are provided including brightness parameter 422 and contrast parameter 424 of the floating viewport. Typical imaging systems have a single brightness and contrast control for the entire medical digital image. In an embodiment of the disclosure, the addition of manual controls 420 for adjusting brightness parameter 422 and contrast parameter 424 of floating viewport 410 provides additional control over the subset image, ROI 408.

An enhanced magnifier tool (for example, enhanced magnifier 316 of FIG. 3) provides a capability of a combination of re-sampling of the sub-region, for example the subset image, ROI 408 within enhanced magnifier 316.

Figure 5:
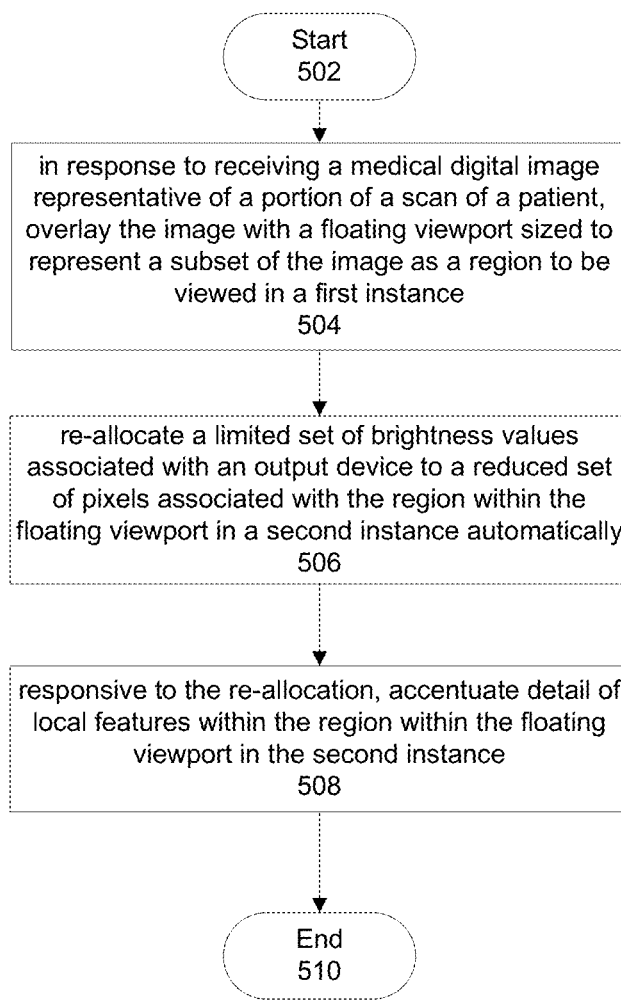
FIG. 5 is a flowchart of a process using the viewport management system 300 of FIG. 3 in accordance with one embodiment of the disclosure.

FIG. 5 is a flowchart of a process using the viewport management system 300 of FIG. 3 in accordance with an embodiment of the disclosure. An embodiment of the disclosure provides a floating viewport as an overlay to an image. Although the examples provided may reference use of a medical digital image in the form of an x-ray scan image, the described process in alternative embodiments is also applicable to other medical image modalities. The region of interest within the floating viewport contains only a subset of all of the data within the medical digital image. This subset image usually contains a fewer number of brightness levels than there are in a number of brightness levels within the medical digital image as a whole. The output device on which the viewport is displayed typically has a range of brightness levels that are less than the number of brightness levels in the subset image, which again is much less than the number of brightness levels in the entire medical digital image.

When a limited set of output brightness levels is re-allocated to the number of brightness levels in the subset image within the area of the floating viewport, rather than the larger number of brightness levels in the entire medical digital image, then contrast within the subset image is greatly enhanced.

Additionally, the window within the viewport can be magnified. Magnification has an effect of further reducing a size of the subset image, and typically the number of brightness levels within that subset.

Process 500, in an example embodiment of automatic viewport re-leveling, begins (step 502) and in response to receiving a medical digital image representative of a portion of a scan of a patient, overlaying the image with a floating viewport sized to represent a subset of the image as a region to be viewed in a first instance, (step 504). The overlay may potentially be magnified in a combination of operations including the overlay.

Process 500, re-allocates a limited set of brightness values associated with an output device to a reduced set of pixels associated with the region within the floating viewport in a second instance automatically, (step 506). Responsive to the re-allocation, process 500 accentuates detail of local features within the region within the floating viewport in the second instance, (step 508) and terminates thereafter (step 510).

By way of example, given a mammography image, represented using a grey scale of approximately 5000×3000 pixels in size, each pixel can represent 16 bits of brightness, or a possible 65,000 brightness/grey levels. However, a display output device can only show 8 bits for any one color (or grey level). With reference to a histogram of the entire mammography image, one can readily determine that most of the available 65,000 brightness levels are used. Some of the pixels are almost completely dark pixels and some of the pixels are very white. Taking one small area on the mammography image, which is neutral gray, that subset image of the mammography image has fewer pixels than the entire mammography image. Therefore, in view of the nature of certain medical images/diagnostics including breast imaging, the subset image of the medical digital image also contains fewer grey levels within the subset image.

With reference to the full mammography image, to fit the full mammography image onto the display screen, pixels are binned to downscale the image. In this case "binned" refers to a technique of assigning one or more values in a predetermined range of values to a "bin" as a means of reducing the number of values to a predetermined set of values that can be process by an output device. A typical example is hashing of the original set of values to a number of predetermined buckets corresponding to a range of values capable of being output by a display device. The same process occurs with the associated brightness levels. As a result, the possible 65000 brightness/grey levels available in the source medical digital image need to be binned and mapped to a much smaller number of output levels, which is typically 8-10 bits per pixel monochrome. The effect of this process reduces or obscures fine details present in the full mammography image.

In contradistinction with typical medical imaging systems, an embodiment of the disclosure re-allocates available output brightness levels (for example, 8 bits) to the now much smaller set of brightness levels in the subset image. The result of this re-allocation is fine brightness details, typically lost when viewing the original full image using a typical medical imaging system, are restored within a potentially magnified subset image of an embodiment of the disclosure.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Thus is presented in an illustrative embodiment a computer-implemented process for automatic viewport re-leveling. The computer-implemented process, in response to receiving a medical digital image, overlays the medical digital image with a floating viewport sized to represent a subset of the image to be viewed in a first instance. A limited set of brightness values is re-allocated to a set of pixels, within the subset of the image in the floating viewport that is less than a set of pixels in the medical digital image, in a second instance automatically. Responsive to the re-allocation, detail of local features within the subset of the image within the floating viewport in the second instance is accentuated.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing a specified logical function. It should also be noted that, in some alternative implementations, the functions noted in the block might occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment, an entirely software embodiment or an embodiment containing both hardware and software elements. In a preferred embodiment, the invention is implemented in software, which includes but is not limited to firmware, resident software, microcode, and other software media that may be recognized by one skilled in the art.

It is important to note that while the present invention has been described in the context of a fully functioning data processing system, those of ordinary skill in the art will appreciate that the processes of the present invention are capable of being distributed in the form of a computer readable data storage device having computer executable instructions stored thereon in a variety of forms. Examples of computer readable data storage devices include recordable-type media, such as a floppy disk, a hard disk drive, a RAM, CD-ROMs, DVD-ROMs. The computer executable instructions may take the form of coded formats that are decoded for actual use in a particular data processing system.

A data processing system suitable for storing and/or executing computer executable instructions comprising program code will include one or more processors coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems, and Ethernet cards are just a few of the currently available types of network adapters.

What is claimed is:

1. A computer-implemented process for automatic viewport re-leveling, the computer-implemented process comprising:
   receiving, with a processor, a medical digital image, the medical digital image including a first set of brightness values allocated to a first set of pixels within the medical digital image;
   in response to receiving the medical digital image, identifying, with the processor, a subset image representing a portion of the medical digital image, wherein the subset image is selected by a user using a floating viewport sized to represent the portion of the medical digital image represented by the subset image;
   allocating, with the processor, a second set of brightness values to a second set of pixels within the subset image, wherein the second set of brightness values includes less brightness values than the first set of brightness values; and
   displaying, with the processor, the subset image with the second set of brightness values, wherein the displayed subset image accentuates detail of local features within the subset image within the floating viewport.

2. The computer-implemented process of claim 1, wherein identifying the subset image representing the portion of the medical digital image includes applying magnification to the medical digital image using an enhanced magnifier tool to enhance spatial detail of only the subset image.

3. The computer-implemented process of claim 1, wherein when a local minima and maxima of the subset image are different from an image-wide minima and maxima of the medical digital image, a dynamic range within the floating viewport is maximized.

4. The computer-implemented process of claim 1, wherein additional manual controls are provided for window/level parameters of the floating viewport, the additional manual controls including a brightness control and a contrast control for use with only the subset image.

5. The computer-implemented process of claim 1, further comprising pre-generating a predetermined number of subset images on a server side, wherein each subset image in the predetermined number of subset images uses a different predetermined combination of brightness control and contrast control.

6. The computer-implemented process of claim 2, wherein applying magnification to the medical digital image to enhance spatial detail of the subset image includes resampling only the subset image identified within the enhanced magnifier tool.

7. The computer-implemented process of claim 1, wherein allocating the second set of brightness values to the second set of pixels within the subset image includes restoring fine brightness details lost in an original full image of the medical digital image.

8. A data processing system for automatic viewport re-leveling, the data processing system comprising:
   a bus;
   a memory connected to the bus, containing computer executable instructions; and
   a processor connected to the bus, wherein the processor executes the computer executable instructions to direct the data processing system to
      receive a medical digital image, the medical digital image including a first set of brightness values allocated to a first set of pixels within the medical digital image,
      in response to receiving the digital medical image, identifying a subset image representing a portion of the medical digital image, wherein the subset image is selected by a user using a floating viewport sized to represent the portion of the medical digital image represented by the subset image,
      allocate a second set of brightness values to a second set of pixels within the subset image, wherein the second set of brightness values includes less brightness values than the first set of brightness values, and
      display the subset image with the second set of brightness values, wherein the displayed subset image accentuates detail of local features within the subset image within the floating viewport.

9. The data processing system of claim 8, wherein the processor executes the computer executable instructions to direct the data processing system to identify the subset image representing the portion of the medical digital image by directing the data processing system to apply magnification to the digital medical image using an enhanced magnifier tool to enhance spatial detail of the subset image.

10. The data processing system of claim 8, wherein when a local minima and maxima of the subset image are different from an image-wide minima and maxima of the digital medical image, a dynamic range within the floating viewport is maximized.

11. The data processing system of claim 8, wherein the processor executes the computer executable instructions to direct the data processing system to provide additional manual controls for window/level parameters of the floating viewport, the additional manual controls including a brightness control and a contrast control for use with the subset image.

12. The data processing system of claim 8, wherein the processor executes the computer executable instructions to direct the data processing system to pre-generate a predetermined number of subset images on a server side, wherein each subset image in the predetermined number of subset images uses a different predetermined combination of brightness control and contrast control.

13. The data processing system of claim 9, wherein the processor executes the computer executable instructions to direct the data processing system to apply magnification to the digital medical image to enhance spatial detail of the subset image by directing the data processing system to re-sample the subset image identified within the enhanced magnifier tool.

14. The data processing system of claim 8, wherein the processor executes the computer executable instructions to direct the data processing system to allocate a second set of brightness values to a second set of pixels within the subset image by directing the data processing system to restore fine brightness details lost in an original full image of the digital medical image.

15. A computer program product for automatic viewport re-leveling, the computer program product comprising a computer readable storage medium having program instructions embodied therewith, the program instructions executable by a computer to cause the computer to:
receiving a medical digital image, the medical digital image including a first set of brightness values allocated to a first set of pixels within the medical digital image;
in response to receiving the digital medical image, identifying a subset image representing a portion of the medical digital image, wherein the subset image is selected by a user using a floating viewport sized to represent the portion of the medical digital image represented by the subset image;
allocating a second set of brightness values to a second set of pixels within the subset image, wherein the second set of brightness values includes less brightness values than the first set of brightness values; and
display the subset image with the second set of brightness values, wherein the displayed subset image accentuates detail of local features within the subset image within the floating viewport.

16. The computer program product of claim 15, wherein the program instructions executable by the computer to cause the computer to identifying the subset image representing the portion of the medical digital image includes causing the computer to apply magnification to the digital medical image using an enhanced magnifier tool to enhance spatial detail of the subset image.

17. The computer program product of claim 15, wherein when a local minima and maxima of the subset image are different from an image-wide minima and maxima of the digital medical image, a dynamic range within the floating viewport is maximized.

18. The computer program product of claim 15, wherein the program instructions executable by the computer further cause the computer to provide additional manual controls for window/level parameters of the floating viewport, the additional manual controls including a brightness control and a contrast control for use with only the subset image.

19. The computer program product of claim 15, wherein the program instructions executable by the computer further cause the computer to pre-generate a predetermined number of subset images on a server side, wherein each subset image in the predetermined number of subset images uses a different predetermined combination of brightness control and contrast control.

20. The computer program product of claim 16, wherein the program instructions executable by the computer to cause the computer to apply magnification to the digital medical image to enhance spatial detail of the subset image includes causing the computer to re-sample the subset image identified within the enhanced magnifier tool.

* * * * *